(12) United States Patent
Inubushi et al.

(10) Patent No.: US 8,592,626 B2
(45) Date of Patent: Nov. 26, 2013

(54) METAL COMPLEX AND MANUFACTURING METHOD THEREFOR

(75) Inventors: Yasutaka Inubushi, Kurashiki (JP); Takashi Hori, Kurashiki (JP); Hiroyuki Ohgi, Kurashiki (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 310 days.

(21) Appl. No.: 13/059,766

(22) PCT Filed: Aug. 19, 2009

(86) PCT No.: PCT/JP2009/064524
§ 371 (c)(1),
(2), (4) Date: May 4, 2011

(87) PCT Pub. No.: WO2010/021345
PCT Pub. Date: Feb. 25, 2010

(65) Prior Publication Data
US 2011/0237796 A1    Sep. 29, 2011

(30) Foreign Application Priority Data

Aug. 19, 2008   (JP) ................. 2008-210581

(51) Int. Cl.
*C07C 63/34*  (2006.01)
*C07C 63/36*  (2006.01)
*B01J 20/26*  (2006.01)

(52) U.S. Cl.
USPC .................... 562/467; 562/490; 502/401

(58) Field of Classification Search
None
See application file for complete search history.

(56) References Cited

U.S. PATENT DOCUMENTS

2003/0121564 A1    7/2003   Taguchi et al.

FOREIGN PATENT DOCUMENTS

| JP | 61 122245    | 6/1986  |
|----|--------------|---------|
| JP | 2003 170294  | 6/2003  |
| JP | 2003 275531  | 9/2003  |
| JP | 2003 278997  | 10/2003 |
| JP | 2003 342260  | 12/2003 |
| JP | 2004 74026   | 3/2004  |
| JP | 2004 161675  | 6/2004  |
| JP | 2003 232222  | 9/2005  |
| JP | 2005 232033  | 9/2005  |
| JP | 2005 232034  | 9/2005  |

OTHER PUBLICATIONS

Lund et al., Journal of the Chemical Society [Section] A: Inorganic, Physical, Theoretical (1971), (13), 2251-3.*

(Continued)

*Primary Examiner* — Karl J Puttlitz
(74) *Attorney, Agent, or Firm* — Oblon, Spivak, McClelland, Maier & Neustadt, L.L.P.

(57) ABSTRACT

Disclosed is a metal complex that can be used as a gas absorption material with superior gas absorbing properties, a gas storage material with a high storage capacity, and a gas separation material with superior gas separation performance and high adsorption capacity. Disclosed is a metal complex, and a manufacturing method therefor, which consists of: a polycyclic aromatic dihydroxy monocarboxylic acid compound, in the structural formula of which hydroxyl groups are at the farthest locations from each other, which has carboxyl groups at the locations adjacent to the hydroxyl groups, and which has 10 or more circularly conjugated π electrons, such as 3,7-dihydorxy-2-naphtoic acid or 4,4'-dihydroxy-3-biphenylcaroxylic acid; at least one metal selected from chromium, molybdenum, tungsten, manganese, iron, ruthenium, cobalt, rhodium, nickel, palladium, copper, zinc, and cadmium; and an organic ligand, such as 4,4'-bipyridyl, capable of bidentate bonding with said metal.

13 Claims, 4 Drawing Sheets (56) References Cited

OTHER PUBLICATIONS

Database Caplus Chemical Abstracts Service, Columbus, Ohio, US; Database Accession No. 1982:624122, Abstract of Dhat et al., Indian Journal of Chemistry, Section A: Inorganic, Physical, Theoretical & Analytical (1982), 21A(8), 792-5.*

Database Caplus Chemical Abstracts Service, Columbus, Ohio, US; Database Accession No. 1964:90069, Abstract of Grossmith BE 631221 Aug. 16, 1963.*

Database Accession No. 1960:101779, Abstract of Pecci et al., Journal of the American Pharmaceutical Association, Scientific Edition (1960), 49, 411-14.*

Uemura, K., et al., Expected Materials for the Future, vol. 2, No. 12, pp. 44-51, (2002).

Kitagawa, S., et al., Petrotech, vol. 26, pp. 97-104, (2003).

International Search Report issued Nov. 17, 2009 in PCT/JP09/064524 filed Aug. 19, 2009.

* cited by examiner

METAL COMPLEX AND MANUFACTURING METHOD THEREFOR

TECHNICAL FIELD

The present invention relates to a metal complex and a manufacturing method therefor. More specifically, it relates to a metal complex composed of an aromatic dihydroxy monocarboxylic acid compound having, in the structural formula thereof, hydroxyl groups located at the farthest positions from each other, having a carboxyl group at a position adjacent to the hydroxyl groups, and having 10 or more circularly conjugated $\pi$ electrons, at least one metal selected from chromium, molybdenum, tungsten, manganese, iron, ruthenium, cobalt, rhodium, nickel, palladium, copper, zinc, and cadmium, and an organic ligand capable of bidentate binding to the metal; and a manufacturing method of the metal complex. The metal complex of the present invention is excellent in adsorption performance of various gases and is preferred as an adsorbent material for adsorbing thereto carbon dioxide, hydrogen, carbon monoxide, oxygen, nitrogen, hydrocarbons having from 1 to 4 carbon atoms, noble gases, hydrogen sulfide, ammonia, sulfur oxide, nitrogen oxide, siloxanes, water vapor, or organic vapor. The metal complex of the present invention is also preferred as a storage material for storing therein carbon dioxide, hydrogen, carbon monoxide, oxygen, nitrogen, hydrocarbons having from 1 to 4 carbon atoms, noble gases, hydrogen sulfide, ammonia, water vapor, or organic vapor. Further, it is also preferred as a separation material for separating carbon dioxide, hydrogen, carbon monoxide, oxygen, nitrogen, hydrocarbons having from 1 to 4 carbon atoms, noble gases, hydrogen sulfide, ammonia, sulfur oxide, nitrogen oxide, siloxanes, water vapor, or organic vapor and it is particularly preferred as a separation material for separating methane from carbon dioxide, hydrogen from carbon dioxide, nitrogen from carbon dioxide, or carbon dioxide from air.

BACKGROUND ART

In the fields of deodorization, exhaust gas treatment and the like, various adsorbent materials have so far been developed. Activated carbon is one of the representative examples of them and it has been used widely in various industries for the purpose of air cleaning, desulfurization, denitrification, or removal of harmful substances by making use of its excellent adsorption performance. In recent years, a demand for nitrogen has been increasing, for example, in the semiconductor manufacturing process and the like. Such nitrogen is produced from the air by using molecular sieving carbon according to the pressure swing adsorption process or temperature swing adsorption process. Molecular sieving carbon is also used for separation and purification of various gases such as purification of hydrogen from a cracked methanol gas.

When a mixture of gases is separated according to the pressure swing adsorption process or temperature swing adsorption process, it is the common practice to separate it based on a difference between the gases in equilibrium adsorption amount or rate of adsorption to molecular sieving carbon or zeolite used as a separation adsorbent material. When the mixture of gases is separated based on a difference in equilibrium adsorption amount, conventional adsorbent materials cannot selectively adsorb thereto only a gas to be removed and a separation coefficient decreases, making it inevitable to increase the size of an apparatus used therefor. When the mixture of gases is separated into individual gases based on a difference in rate of adsorption, on the other hand, only a gas to be removed can be adsorbed, though depending on the kind of the gas. It is necessary, however, to alternately carry out adsorption and desorption and also in this case, the apparatus used therefor should have an increased size.

On the other hand, there has also been developed, as an adsorbent material providing superior adsorption performance, a coordination polymer undergoing a change in dynamic structure when exposed to external stimulation (refer to Non-patent Documents 1 and 2). When this novel coordination polymer undergoing a change in dynamic structure is used as a gas adsorbent material, it does not adsorb a gas until a predetermined pressure but it starts gas adsorption at a pressure exceeding the predetermined pressure. In addition, a phenomenon is observed in which an adsorption starting pressure differs depending on the nature of the gas.

Application of these phenomena to adsorbent materials used in a gas separation apparatus employing a pressure swing adsorption system enables very efficient gas separation. It can also decrease time required for pressure change, contributing to energy saving. Further, it can contribute to a size reduction of the gas separation apparatus, making it possible to increase competitiveness in terms of cost when a high-purity gas is put on the market as a product. To say nothing of it, even if the high purity gas is used in the own plant, the cost paid for the equipment requiring a high purity gas can be reduced, resulting in a reduction effect of a manufacturing cost of the final product.

There are known, as a using example of a coordination polymer undergoing a change in dynamic structure as a storage material or a separation material, (1) a metal complex having an interdigitated framework (refer to Patent Document 1), (2) a metal complex having a two-dimensional square-grid framework (refer to Patent Documents 2, 3, and 4), and (3) a metal complex having an interpenetrated framework (refer to Patent Document 5).

At present, however, it is requested to reduce the using amount of an adsorbent material in order to reduce the size of an apparatus, thereby achieving cost reduction. Although a further increase in the adsorption capacity is requested to achieve it, none of these related arts refers to an increase in the adsorption capacity. As a result of measurement at 273 K of an equilibrium adsorption amount of carbon dioxide to the metal complexes disclosed in Patent Document 1 to 4, it is about 80 mL (STP)/g and the amount of the metal complex described in Patent Document 5 is less than about 100 mL (STP)/g at most.

It is on the other hand known that some of the metal complexes having a two-dimensional square-grid framework have a large adsorption capacity (refer to Patent Documents 6, 7, and 8). These complexes, however, contain a tetrafluoroborate ion or trifluoromethanesulfonate ion and corrosion of a reaction container used in their manufacture or treatment of waste liquids upon manufacture poses a problem. They are therefore not suited for industrial manufacture. In addition, none of these coordination polymers starts adsorption of a gas until it exceeds a predetermined pressure so that when the partial pressure of a gas to be removed by adsorption from a mixture of gases is below the predetermined pressure, adsorption does not occur. An increase in the using amount of the metal complex is therefore inevitable to obtain a high purity gas and under such a situation, it is difficult to reduce the size of the apparatus.

PRIOR ART DOCUMENTS

Patent Document

[Patent Document 1] Japanese Patent Laid-Open No. 2004-161675
[Patent Document 2] Japanese Patent Laid-Open No. 2003-275531
[Patent Document 3] Japanese Patent Laid-Open No. 2003-278997
[Patent Document 4] Japanese Patent Laid-Open No. 2005-232222

[Patent Document 5] Japanese Patent Laid-Open No. 2003-342260
[Patent Document 6] Japanese Patent Laid-Open No. 2004-74026
[Patent Document 7] Japanese Patent Laid-Open No. 2005-232033
[Patent Document 8] Japanese Patent Laid-Open No. 2005-232034

Non-Patent Documents

[Non-patent Document 1] Kazuhiro Uemura and Susumu Kigatawa, "Expected Materials for the Future", 2, 44 to 51(2002)
[Non-patent Document 2] Ryotaro Matsuda and Susumu Kitagawa, "PETROTECH", 26, 97 to 104(2003)

DISCLOSURE OF THE INVENTION

Problems that the Invention is to Solve

An object of the invention is therefore to provide a metal complex that can be used as an adsorbent material having gas adsorption properties superior to those of conventional adsorbent materials, a gas storage material having an effective storage amount greater than that of conventional storage materials, and a gas separation material having a large adsorption amount.

Means for Solving the Problems

The present inventors have carried out an intensive investigation. As a result, it has been found that the above object can be achieved by a metal complex composed of an aromatic dihydroxy monocarboxylic acid compound having hydroxyl groups at the farthest positions from each other in the structural formula of the aromatic dihydroxy monocarboxylic acid, having a carboxyl group at a position adjacent to the hydroxyl group, and having 10 or more circularly conjugated π electrons, at least one metal selected from chromium, molybdenum, tungsten, manganese, iron, ruthenium, cobalt, rhodium, nickel, palladium, copper, zinc, and cadmium, and an organic ligand capable of bidentate binding to the metal, leading to the completion of the invention.

The followings are provided by the invention.

(1) A metal complex composed of an aromatic dihydroxy monocarboxylic acid compound having hydroxyl groups at the farthest positions from each other in the structural formula of the aromatic dihydroxy monocarboxylic acid compound, having a carboxyl group at a position adjacent to the hydroxyl group, and having 10 or more circularly conjugated π electrons, at least one metal selected from chromium, molybdenum, tungsten, manganese, iron, ruthenium, cobalt, rhodium, nickel, palladium, copper, zinc, and cadmium, and an organic ligand capable of bidentate binding to the metal.

(2) The metal complex as described above in (1), wherein the aromatic dihydroxy monocarboxylic acid compound is represented by the following formula (I):

[Chemcial formula 1]

(I)

(where, $R^1$, $R^2$, $R^3$, $R^4$ and $R^5$ may be the same or different and each independently represents a hydrogen atom, an alkyl group which may have a substituent, an aryl group, an aralkyl group, an alkoxy group, an aryloxy group, an aralkyloxy group, an amino group, an amide group, or a halogen atom), at least one metal selected from chromium, molybdenum, tungsten, manganese, iron, ruthenium, cobalt, rhodium, nickel, palladium, copper, zinc, and cadmium, and an organic ligand capable of bidentate binding to the metal.

(3) The metal complex as described above in (1), wherein the aromatic dihydroxy monocarboxylic acid compound is represented by the following formula (II):

[Chemical formula 2]

(II)

(where, $R^6$, $R^7$, $R^8$, $R^9$, $R^{10}$, $R^{11}$ and $R^{12}$ may be the same or different and each independently represents a hydrogen atom, an alkyl group which may have a substituent, an aryl group, an aralkyl group, an alkoxy group, an aryloxy group, an aralkyloxy group, an amino group, an amide group, or a halogen atom), at least one metal selected from chromium, molybdenum, tungsten, manganese, iron, ruthenium, cobalt, rhodium, nickel, palladium, copper, zinc, and cadmium, and an organic ligand capable of bidentate binding to the metal.

(4) The metal complex as described above in (1), wherein the organic ligand capable of bidentate binding to the metal is at least one selected from 1,4-diazabicyclo[2.2.2]octane, pyrazine, 2,5-dimethylpyrazine, 4,4'-bipyridyl, 2,2'-dimethyl-4,4'-bipyridine, 1,2-bis(4-pyridyl)ethyne, 1,4-bis(4-pyridyl)butadiyne, 1,4-bis(4-pyridyl)benzene, 3,6-di(4-pyridyl)-1,2,4,5-tetrazine, 2,2'-bi-1,6-naphthyridine, phenazine, diazapyrene, trans-1,2-bis(4-pyridyl)ethene, 4,4'-azopyridine, 1,2-bis(4-pyridyl)ethane, 1,2-bis(4-pyridyl)glycol, and N-(4-pyridyl)isonicotinamide.

(5) The metal complex as described above in (2), wherein the aromatic dihydroxy monocarboxylic acid compound (I) is 3,7-dihydroxy-2-naphthoic acid.

(6) The metal complex as described above in (3), wherein the aromatic dihydroxy monocarboxylic acid compound (II) is 4,4'-dihydroxy-3-biphenylcarboxylic acid.

(7) The metal complex as described above in (1), wherein the metal is copper.

(8) An adsorbent material composed of the metal complex as described above in (1).

(9) The adsorbent material as described above in (8), which is an adsorbent material for adsorbing thereto carbon dioxide, hydrogen, carbon monoxide, oxygen, nitrogen, hydrocarbons having from 1 to 4 carbon atoms, noble gases, hydrogen sulfide, ammonia, sulfur oxide, nitrogen oxide, siloxanes, water vapor, or organic vapor;

(10) A storage material composed of the metal complex as described above in (1).

(11) The storage material as described above in (10), which is a storage material for storing therein carbon dioxide, hydrogen, carbon monoxide, oxygen, nitrogen, hydrocarbons having from 1 to 4 carbon atoms, noble gases, hydrogen sulfide, ammonia, water vapor, or organic vapor.

(12) A separation material composed of the metal complex as described above in (1).

(13) The separation material as described above in (12), which is a separation material for separating carbon dioxide, hydrogen, carbon monoxide, oxygen, nitrogen, hydrocarbons having from 1 to 4 carbon atoms, noble gases, hydrogen sulfide, ammonia, sulfur oxide, nitrogen oxide, siloxanes, water vapor, or organic vapor.

(14) The separation material as described above in (12), which is a separation material for separating methane from carbon dioxide, hydrogen from carbon dioxide, nitrogen from carbon dioxide, or carbon dioxide from air.

(15) A manufacturing method of the metal complex as described above in (1), including a step of reacting, in a solvent, an aromatic dihydroxy monocarboxylic acid compound having hydroxyl groups at the farthest positions from each other in the structural formula of the aromatic dihydroxy monocarboxylic acid compound, having a carboxyl group at a position adjacent to the hydroxyl group, and having 10 or more circularly conjugated π electrons, at least one metal salt selected from chromium salt, molybdenum salt, tungsten salt, manganese salt, iron salt, ruthenium salt, cobalt salt, rhodium salt, nickel salt, palladium salt, copper salt, zinc salt, and cadmium salt, and an organic ligand capable of bidentate binding to the metal to cause precipitation.

Effect of the Invention

The invention can provide a metal complex composed of an aromatic dihydroxy monocarboxylic acid compound having hydroxyl groups at the farthest positions from each other in the structural formula of the aromatic dihydroxy monocarboxylic acid compound, having a carboxyl group at a position adjacent to the hydroxyl group, and having 10 or more circularly conjugated π electrons, at least one metal selected from chromium, molybdenum, tungsten, manganese, iron, ruthenium, cobalt, rhodium, nickel, palladium, copper, zinc, and cadmium, and an organic ligand capable of bidentate binding to the metal.

The metal complex of the invention is excellent in adsorption performance of various gases so that it can be used as an adsorbent material for adsorbing thereto carbon dioxide, hydrogen, carbon monoxide, oxygen, nitrogen, hydrocarbons having from 1 to 4 carbon atoms, noble gases, hydrogen sulfide, ammonia, sulfur oxide, nitrogen oxide, siloxanes, water vapor, or organic vapor.

The metal complex of the invention shows a peculiar gate opening type adsorption behavior in which an adsorption amount increases drastically at a pressure exceeding a certain predetermined pressure equal to or greater than the normal pressure (0.1 MPa) so that it can be used as a storage material having a large effective adsorption amount. Examples of the gases to be stored include carbon dioxide, hydrogen, carbon monoxide, oxygen, nitrogen, hydrocarbons having from 1 to 4 carbon atoms, noble gases, hydrogen sulfide, ammonia, water vapor, and organic vapor.

Further, the metal complex of the invention can be used as a separation material for separating carbon dioxide, hydrogen, carbon monoxide, oxygen, nitrogen, hydrocarbons having from 1 to 4 carbon atoms, noble gases, hydrogen sulfide, ammonia, sulfur oxide, nitrogen oxide, siloxanes, water vapor, or organic vapor by making use the phenomenon that a pressure at which an adsorption amount shows a drastic increase differs, depending on the nature of the gas. In particular, it can be used as a separation material for separating methane from carbon dioxide, hydrogen from carbon dioxide, nitrogen from carbon dioxide, or carbon dioxide from air. The metal complex shows a two-step adsorption behavior, that is, a continuous change from an adsorption behavior classified as Type I in the IUPAC classification to a gate opening type adsorption behavior, depending on an increase in the adsorption pressure so that when the metal complex is used, for example, in a pressure swing adsorption process, not only a high recovery rate but also high achieving purity and implementation of a recovery step under ordinary pressure can also be expected.

MODE FOR CARRYING OUT THE INVENTION

The metal complex of the invention is composed of an aromatic dihydroxy monocarboxylic acid compound having hydroxyl groups at the farthest positions from each other in the structural formula of the aromatic dihydroxy monocarboxylic acid compound, having a carboxyl group at a position adjacent to the hydroxyl group, and having 10 or more circularly conjugated π electrons and at least one metal selected from chromium, molybdenum, tungsten, manganese, iron, ruthenium, cobalt, rhodium, nickel, palladium, copper, zinc, and cadmium, and an organic ligand capable of bidentate binding to the metal.

The metal complex of the invention can be obtained by reacting an aromatic dihydroxy monocarboxylic acid compound having hydroxyl groups at the farthest positions from each other in the structural formula of the aromatic dihydroxy monocarboxylic acid compound, having a carboxyl group at a position adjacent to the hydroxyl group, and having 10 or more circularly conjugated π electrons and at least one metal salt selected from chromium salt, molybdenum salt, tungsten salt, manganese salt, iron salt, ruthenium salt, cobalt salt, rhodium salt, nickel salt, palladium salt, copper salt, zinc salt, and cadmium salt, and an organic ligand capable of bidentate binding to the metal for several hours to several days in a solvent under ordinary pressure to cause precipitation. It can be obtained, for example, by mixing a solution of a metal salt in water or an organic solvent with an organic solvent solution containing an aromatic dihydroxy monocarboxylic acid compound and an organic ligand capable of bidentate binding under ordinary pressure and thereby reacting the resulting mixture.

The aromatic hydrocarbon ring portion obtained by removing from the aromatic dihydroxy monocarboxylic acid compound two hydroxyl groups, one carboxyl group, and $R^1$ to $R^{12}$ is preferably polycyclic. Examples of the polycyclic aromatic hydrocarbon ring include naphthalene, azulene, phenanthrene, anthracene, triphenylene, chrysene, naphthacene, picene, pentaphene, pentacene, biphenyl, and terphenyl. Of these, naphthalene and biphenyl are preferred. The term "having hydroxyl groups at the farthest positions from each other in the structural formula of the aromatic dihydroxy monocarboxylic acid compound" means a positional relationship under which a straight-line distance between carbon atoms having two hydroxyl groups bound thereto is the longest. For example in naphthalene, two hydroxyl groups are in a 2,6 positional relationship or 3,7 positional relationship with each other, while in biphenyl, they are in a 4,4' positional relationship with each other.

The number of circularly conjugated π electrons of the aromatic dihydroxy monocarboxylic acid compound means the number of conjugated π electrons present in the aromatic hydrocarbon ring of the aromatic dihydroxy monocarboxylic acid compound other than two hydroxyl groups, one carboxyl group, and $R^1$ to $R^{12}$ thereof, and it is preferably from 10 to 22. Using an aromatic dihydroxy monocarboxylic acid compound having less than 10π electrons may lead to preparation of a metal complex having a reduced adsorption amount, reduced storage amount, and reduced separation performance, while using an aromatic dihydroxy monocarboxylic acid compound having greater than 24π electrons may lead to preparation of a metal complex having reduced stability and reduced crystallinity at a reduced yield.

Preferred examples of the aromatic dihydroxy monocarboxylic acid compound include compounds represented by the following formulas (I) and (II);

[Chemical formula 3]

(I)

[Chemical formula 4]

(II)

In the above formulas, $R^1$, $R^2$, $R^3$, $R^4$, $R^5$, $R^6$, $R^7$, $R^8$, $R^9$, $R^{10}$, $R^{11}$ and $R^{12}$ may be the same or different and each independently represents a hydrogen atom, an alkyl group which may have a substituent, an aryl group, an aralkyl group, an alkoxy group, an aryloxy group, an aralkyloxy group, an amino group, an amide group, or a halogen atom.

The above alkyl group has preferably from 1 to 5 carbon atoms. Examples of the alkyl group include linear or branched alkyl groups such as methyl, ethyl, n-propyl, isopropyl, n-butyl, isobutyl, tert-butyl, and pentyl; those of the halogen atom include fluorine atom, chlorine atom, bromine atom, and iodine atom; those of the aryl group include phenyl group; those of the aralkyl group include benzyl group; those of the alkoxy group include methoxy, ethoxy, n-propoxy, isopropoxy, n-butoxy, isobutoxy, and tert-butoxy; those of the aryloxy group include phenoxy group; those of the aralkyloxy group include benzyloxy group; and those of the amino group include N,N-dimethylamino group. Examples of the substituent which the alkyl group may have include alkoxy groups (such as methoxy, ethoxy, n-propoxy, isopropoxy, n-butoxy, isobutoxy, and tert-butoxy), amino group, aldehyde group, epoxy group, acyloxy groups (such as acetoxy, n-propanoyloxy, n-butanoyloxy, pivaloyloxy, and benzoyloxy), alkoxycarbonyl groups (such as methoxycarbonyl, ethoxycarbonyl, and n-butoxycarbonyl), and carboxylic anhydride groups (—CO—O—CO—R groups in which R represents an alkyl group having from 1 to 5 carbon atoms). The number of the substituent of the alkyl group is preferably from 1 to 3, more preferably 1.

The aromatic dihydroxy monocarboxylic acid compound is preferably 3,7-dihydroxy-2-naphthoic acid, 2,6-dihydroxy-1-naphthoic acid, or 4,4'-dihydroxy-3-biphenylcarboxylic acid, more preferably 3,7-dihydroxy-2-naphthoic acid or 4,4'-dihydroxy-3-biphenylcarboxylic acid.

The molar concentration of the aromatic dihydroxy monocarboxylic acid compound is preferably from 0.01 to 1.0 mol/L, more preferably from 0.05 to 0.6 mol/L. The reaction at concentrations less than the above range can produce the target metal complex, but is not preferred because it leads to a reduction in yield. On the other hand, the reaction at concentrations exceeding the above range does not proceed smoothly due to a reduction in solubility.

With regard to a mixing ratio of the aromatic dihydroxy monocarboxylic acid compound and the organic ligand capable of bidentate binding, an (aromatic dihydroxy monocarboxylic acid compound):(organic ligand capable of bidentate binding) molar ratio falls within a range of preferably from 1:5 to 8:1, more preferably from 1:3 to 6:1. Even the reaction outside the above range can produce the target metal complex, but is not preferred because it leads to a reduction in yield and an increase in side reactions.

With regard to a mixing ratio of the metal salt and the organic ligand capable of bidentate binding, a (metal salt):(organic ligand capable of bidentate binding) molar ratio falls within a range of preferably from 3:1 to 1:3, more preferably from 2:1 to 1:2. Molar ratios outside the above range reduce a production yield of the target metal complex and make it difficult to purify the metal complex thus obtained due to remaining of unreacted raw materials.

As the organic ligand capable of bidentate binding, those selected from 1,4-diazabicyclo[2.2.2]octane, pyrazine, 2,5-dimethylpyrazine, 4,4'-bipyridyl, 2,2'-dimethyl-4,4'-bipyridine, 1,2-bis(4-pyridyl)ethyne, 1,4-bis(4-pyridyl)butadiyne, 1,4-bis(4-pyridyl)benzene, 3,6-di(4-pyridyl)-1,2,4,5-tetrazine, 2,2'-bi-1,6-naphthyridine, phenazine, diazapyrene, trans-1,2-bis(4-pyridyl)ethene, 4,4'-azopyridine, 1,2-bis(4-pyridyl)ethane, 1,2-bis(4-pyridyl)glycol, and N-(4-pyridyl) isonicotinamide can be used. Of these, 4,4'-bipyridyl is preferred.

The molar concentration of the organic ligand capable of bidentate binding is preferably from 0.002 to 0.5 mol/L, more preferably from 0.02 to 0.3 mol/L. Molar concentrations less than the above range are not preferred because of a reduction in production yield, though the target metal complex can be obtained. Molar concentrations exceeding the above range, on the other hand, reduce the solubility and prevent smooth progress of the reaction.

As the metal salt, those selected from chromium salts, molybdenum salts, tungsten salts, manganese salts, iron salts, ruthenium salts, cobalt salts, rhodium salts, nickel salts, palladium salts, copper salts, zinc salts, and cadmium salts can be used. Of these, copper salts are preferred. As these metal salts, organic acid salts such as acetate and formate and inorganic acid salts such as sulfate, nitrate, and carbonate can be used.

The molar concentration of the metal salt is preferably from 0.001 to 0.25 mol/L, more preferably from 0.01 to 0.15 mol/L. Molar concentrations less than the above range are not preferred because of a reduction in production yield, though the target metal complex can be obtained. Molar concentrations exceeding the above range, on the other hand, make it difficult to purify the metal complex thus obtained due to remaining of an unreacted metal salt.

As the solvent, organic solvents and water, and mixed solvents thereof can be used. Specific examples include methanol, ethanol, propanol, diethyl ether, dimethoxyethane, tetrahydrofuran, hexane, cyclohexane, heptane, benzene, toluene, methylene chloride, chloroform, acetone, ethyl acetate, acetonitrile, N,N-dimethylformamide, and water, and mixed solvents thereof. The reaction temperature is preferably from 253 to 373 K. The reaction occurs even at normal temperature.

The metal complex having superior crystallinity has high purity and has a good adsorption performance. The completion of the reaction can be confirmed by analyzing the remaining amount of the raw materials by using gas chromatography or high-performance liquid chromatography. The metal complex of the invention can be obtained by, after completion of the reaction, subjecting the resulting mixed solution to suction filtration to collect precipitates, washing them with an organic solvent, and then vacuum drying at about 373 K for several hours.

The metal complex of the invention thus obtained has a three-dimensional structure having pores (one-dimensional channels) in which two-dimensional sheets obtained by connecting one-dimensional chains having the oxygen of the carboxyl group and the oxygen of two hydroxyl groups in the aromatic dihydroxy monocarboxylic acid compound coordinated to metal ions (for example, copper ions) to each other via a bidentate ligand have been integrated.

The three-dimensional structure of the metal complex of the invention can also change in the crystal form after synthesis so that with this change, the structure or the size of pores also changes. Conditions causing this structural change depend on the kind of a substance to be adsorbed, adsorption pressure, or adsorption temperature. This means that the degree of the structural change differs with a substance to be adsorbed as well as a difference in the interaction between the pore surface and the substance (the intensity of the interaction is in proportion to the magnitude of a Lennard-Jones potential of the substance), which leads to a high selectivity. The pores increase in size in such a way and large molecules are adsorbed to the pores having an increased size. After desorption of the adsorbed substance, the structure of the metal complex returns to the original one so that the size of the pores also returns to the original one. In addition, the metal complex of the invention has two kinds of pores, that is, ordinarily accessible pores and pores opening at at least a predetermined pressure so that it exhibits a two-step adsorption behavior.

The above adsorption mechanism is an estimated one. Even if an adsorption mechanism does not conform to the above mechanism, it will be embraced within the technical scope of the invention insofar as it satisfies the requirements specified in the invention.

The metal complex of the invention undergoes a change in an integrated structure thereof and also in the size of pores, depending on the kind of a substance to be adsorbed, adsorption pressure, or adsorption temperature so that its adsorption amount increases drastically and reaches the maximum amount as soon as the pressure reaches a predetermined value. The pressure differs depending on the kind of a substance to be adsorbed or adsorption temperature.

Various gases are adsorbed to the metal complex. Examples include carbon dioxide, hydrogen, carbon monoxide, oxygen, nitrogen, hydrocarbons having from 1 to 4 carbon atoms (such as methane, ethane, ethylene, and acetylene), noble gases (such as helium, neon, argon, krypton, and xenon), hydrogen sulfide, ammonia, sulfur oxide, nitrogen oxide, siloxanes (hexamethylcyclotrisiloxane and octamethylcyclotetrasiloxane), water vapor, and organic vapor. The term "organic vapor" means a vaporizing gas of an organic substance which is in liquid form at ordinary temperature under ordinary pressure. Examples of such an organic substance include alcohols such as methanol and ethanol, amines such as trimethylamine, aldehydes such as acetaldehyde, aliphatic hydrocarbons having from 5 to 16 carbon atoms, aromatic hydrocarbons such as benzene and toluene, ketones such as acetone and methyl ethyl ketone, and halogenated hydrocarbons such as methyl chloride and chloroform.

The metal complex of the invention undergoes a change in an integrated structure thereof and also in the size of pores, depending on the kind of a substance to be stored, storage pressure, or storage temperature so that its storage amount increases drastically and reaches the maximum storage amount as soon as the pressure reaches a predetermined value. The pressure differs depending on the kind of a substance to be stored or storage temperature.

Various gases are stored in the metal complex. Examples include carbon dioxide, hydrogen, carbon monoxide, oxygen, nitrogen, hydrocarbons having from 1 to 4 carbon atoms (such as methane, ethane, ethylene, and acetylene), noble gases (such as helium, neon, argon, krypton, and xenon), hydrogen sulfide, ammonia, water vapor, and organic vapor. The term "organic vapor" means a vaporizing gas of an organic substance which is in liquid form at ordinary temperature under ordinary pressure. Examples of such an organic substance include alcohols such as methanol and ethanol, amines such as trimethylamine, aldehydes such as acetaldehyde, aliphatic hydrocarbons having from 5 to 16 carbon atoms, aromatic hydrocarbons such as benzene and toluene, ketones such as acetone and methyl ethyl ketone, and halogenated hydrocarbons such as methyl chloride and chloroform.

Further, the metal complex of the invention can selectively adsorb thereto various gases by controlling the adsorption pressure so that it is preferred as a separation material for separating carbon dioxide, hydrogen, carbon monoxide, oxygen, nitrogen, hydrocarbons having from 1 to 4 carbon atoms (such as methane, ethane, ethylene, or acetylene), noble gases (such as helium, neon, argon, krypton, or xenon), hydrogen sulfide, ammonia, sulfur oxide, nitrogen oxide, a siloxanes (hexamethylcyclotrisiloxane or octamethylcyclotetrasiloxane), water vapor, and organic vapor. In particular, it is suited for separating methane from carbon dioxide, hydrogen from carbon dioxide, nitrogen from carbon dioxide, or carbon dioxide from air by using a pressure swing adsorption process or a temperature swing adsorption process. The term "organic vapor" means a vaporizing gas of an organic substance which is in liquid form at ordinary temperature and ordinary pressure. Examples of such an organic substance include alcohols such as methanol and ethanol, amines such as trimethylamine, aldehydes such as acetaldehyde, aliphatic hydrocarbons having from 5 to 16 carbon atoms, aromatic hydrocarbons such as benzene and toluene, ketones such as methyl ethyl ketone, and halogenated hydrocarbons such as methyl chloride and chloroform.

EXAMPLES

The invention will hereinafter be described specifically by Examples. It should be borne in mind, however, that the invention is not limited to or by them. The analysis and evaluation in the following Examples and Comparative Examples were conducted as described below.
(1) Measurement of Powder X-Ray Diffraction Pattern The powder X-ray diffraction pattern was measured with an X-ray diffractometer based on the symmetric reflection method while scanning at a scanning rate of 1°/min within a diffraction angle (2θ) range of from 5 to 50°. Details of the measurement conditions are shown below.
<Analysis Conditions>
Apparatus: "RINT-2400" trade name; product of Rigaku Corporation
X-ray source: Cu Kα ($\lambda$=1.5418 Å) 40 kV 200 mA
Goniometer: vertical goniometer
Detector: scintillation counter
Step width: 0.02°
Slit:divergence slit=0.5°
  receiving slit=0.15 mm
  scattering slit=0.5°
(2) Measurement of Adsorption/Desorption Isotherm An adsorption/desorption isotherm was measured based on the volumetric method by using a high-pressure gas adsorption measuring instrument. Prior to the measurement, the sample was dried at 373 K and 50 Pa for 10 hours to remove adsorbed water and the like. The following are details of the measurement conditions.
<Measurement Conditions>
Apparatus: "BELSORP-HP", trade name; product of Bel Japan, Inc.
Equilibrium waiting time: 500 sec.
(3) Measurement of Mixed Gas Separation Performance A 10 mL round bottom two-necked glass flask equipped with a three-way cock and a septum was prepared. A 100 mL syringe was connected with a tube to one of the openings of the three-way cock via another three-way cock. Measurement was performed by charging the two-necked flask with a sample, drying at 373 K and $4.0 \times 10^{-3}$ Pa for 3 hours to remove adsorbed water and the like, closing the three-way cock which the flask was equipped with, introducing 100 mL of a gas mixture to the syringe through the three-way cock on the side of the syringe, and finally opening the three-way cock which the flask was equipped with to adsorb the gas mixture to the sample. The adsorption amount at that time was calculated from a decrease of the scale of the syringe (dead volume was measured in advance by using helium) and the gas composition was analyzed using gas chromatography. Details of the measurement conditions will next be described.

<Analysis Conditions>
Apparatus: "GC-14B", trade name; product of Shimadzu Corporation
Column: trade name; product of GL Sciences, Inc.
INJ temperature: 100° C.
DET temperature: 50° C.
Column temperature: 50° C.
Carrier gas: helium
Injection amount: 1 mL
Detector: TCD Synthesis Example 1

Figure 1:
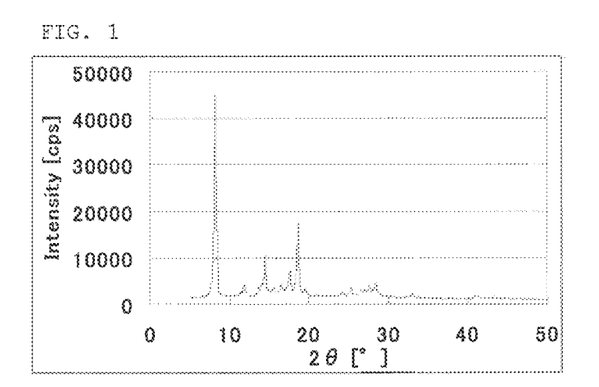
FIG. 1 A powder X-ray diffraction pattern of a metal complex obtained in Synthesis Example 1.

Under nitrogen atmosphere, a 200 mL solution of 4,4'-bipyridyl having a concentration of 0.08 mol/L and a 200 mL solution of 3,7-dihydroxy-2-naphthoic acid having a concentration of 0.32 mol/L, each dissolved in acetone, were added dropwise to 100 mL (0.04 mol/L) of an aqueous solution of copper acetate over 1 hour. The resulting mixture was then stirred at 298 K for 2 hours. After suction filtration, washing was performed three times with acetone, followed by drying at 373 K and 50 Pa for 8 hours to obtain 4.61 g (yield: 92%) of the target metal complex. The powder X-ray diffraction pattern of the metal complex thus obtained is shown in FIG. 1.

Synthesis Example 2

Figure 2:
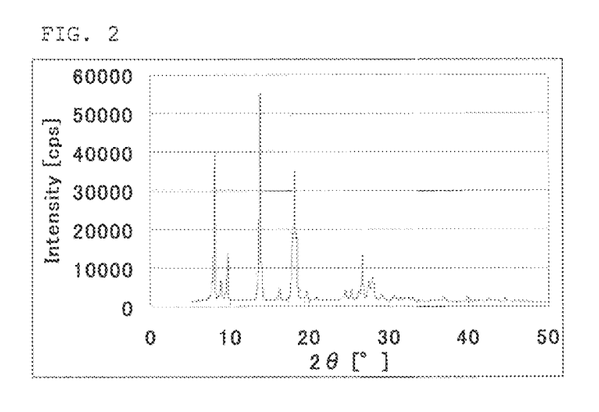
FIG. 2 A powder X-ray diffraction pattern of a metal complex obtained in Synthesis Example 2.

Under nitrogen atmosphere, 200 mL of a solution of 4,4'-bipyridyl having a concentration of 0.08 mol/L and 200 mL of a solution of 4,4'-dihydroxy-3-biphenylcarboxylic acid having a concentration of 0.32 mol/L, each dissolved in acetone, were added dropwise to 100 mL (0.04 mol/L) of an aqueous solution of copper acetate over 1 hour. The resulting mixture was then stirred at 298 K for 2 hours. After suction filtration, washing was performed three times with acetone, followed by drying at 373 K and 50 Pa for 8 hours to obtain 4.80 g (yield: 88%) of the target metal complex. The powder X-ray diffraction pattern of the metal complex thus obtained is shown in FIG. 2.

Comparative Synthesis Example 1

Figure 3:
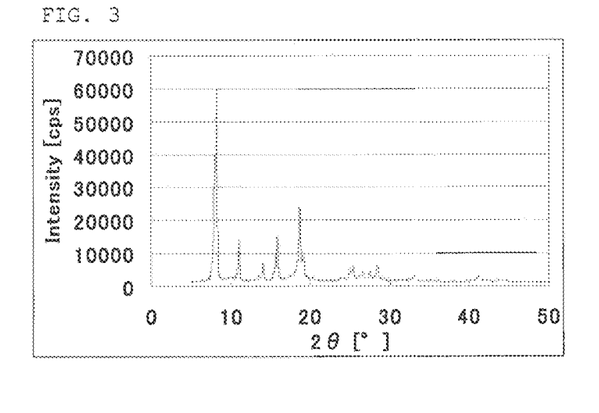
FIG. 3 A powder X-ray diffraction pattern of a metal complex obtained in Comparative Synthesis Example 1.

Under nitrogen atmosphere, 200 mL of a solution of 4,4'-bipyridyl having a concentration of 0.08 mol/L and a 200 mL of a solution of 2,5-dihydroxybenzoic acid having a concentration of 0.32 mol/L, each dissolved in acetone, were added dropwise to 100 mL (0.04 mol/L) of an aqueous solution of copper acetate over 1 hour. The resulting mixture was then stirred at 298 K for 2 hours. After suction filtration, washing was performed three times with acetone, followed by drying at 373 K and 50 Pa for 8 hours to obtain 3.66 g (yield: 87%) of the target metal complex. The powder X-ray diffraction pattern of the metal complex thus obtained is shown in FIG. 3.

Comparative Synthesis Example 2

Under nitrogen atmosphere, 200 mL of a solution of 4,4'-bipyridyl having a concentration of 0.08 mol/L and 200 mL of a solution of 1,4-dihydroxy-2-naphthoic acid having a concentration of 0.32 mol/L, each dissolved in acetone, were added dropwise to 100 mL (0.04 mol/L) of an aqueous solution of copper acetate over 1 hour. The resulting mixture was then stirred at 298 K for 2 hours. After suction filtration, washing was performed three times with acetone, followed by drying at 373 K and 50 Pa for 8 hours to obtain 3.02 g (yield: 60%) of the target metal complex. As a result of measurement of the powder X-ray diffraction pattern of the metal complex thus obtained, it was found that due to the use of an aromatic dihydroxy monocarboxylic acid compound having hydroxyl groups at positions close to each other, the metal complex thus obtained was an amorphous powder and the target three-dimensional structure was not constructed.

Comparative Synthesis Example 3

Figure 4:
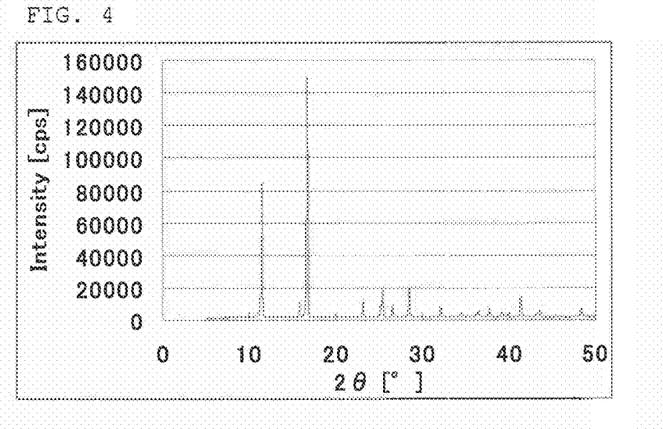
FIG. 4 A powder X-ray diffraction pattern of a metal complex obtained in Comparative Synthesis Example 2.

Under nitrogen atmosphere, 5.00 g (32 mmol) of 4,4'-bipyridyl was dissolved in 400 mL of methanol and the resulting solution was heated to 343 K. Then, 200 mL of an aqueous solution of 3.79 g (16 mmol) of copper tetrafluoroborate was added dropwise over 20 minutes. The resulting mixture was stirred at 343 K for 1 hour. After suction filtration, washing was performed three times with methanol to obtain 2.16 g (yield: 23%) of the target metal complex. The powder X-ray diffraction pattern of the resulting metal complex is shown in FIG. 4.

Example 1

Figure 5:
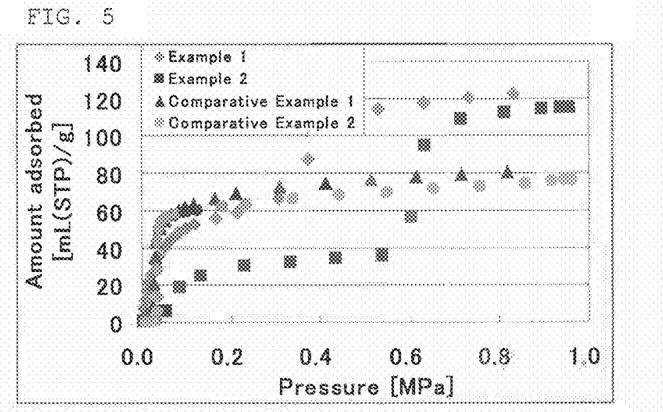
FIG. 5 The results of measuring, by using the volumetric method, adsorption isotherms for carbon dioxide at 273 K of the metal complexes obtained in Synthesis Example 1, Synthesis Example 2, Comparative Synthesis Example 1, and Comparative Synthesis Example 2.

An adsorption isotherm for carbon dioxide at 273 K of the metal complex obtained in Synthesis Example 1 was measured based on the volumetric method. The results are shown in FIG. 5.

Example 2

An adsorption isotherm for carbon dioxide at 273 K of the metal complex obtained in Synthesis Example 2 was measured based on the volumetric method. The results are shown in FIG. 5.

Comparative Example 1

An adsorption isotherm for carbon dioxide at 273 K of the metal complex obtained in Comparative Synthesis Example 1 was measured based on the volumetric method. The results are shown in FIG. 5.

Comparative Example 2

An adsorption isotherm for carbon dioxide at 273 K of the metal complex obtained in Comparative Synthesis Example 3 was measured based on the volumetric method. The results are shown in FIG. 5.

It is apparent from FIG. 5 that the metal complexes of the invention are excellent as an adsorbent material of carbon dioxide because an equilibrium adsorption amount of carbon dioxide is large.

Example 3

Figure 6:
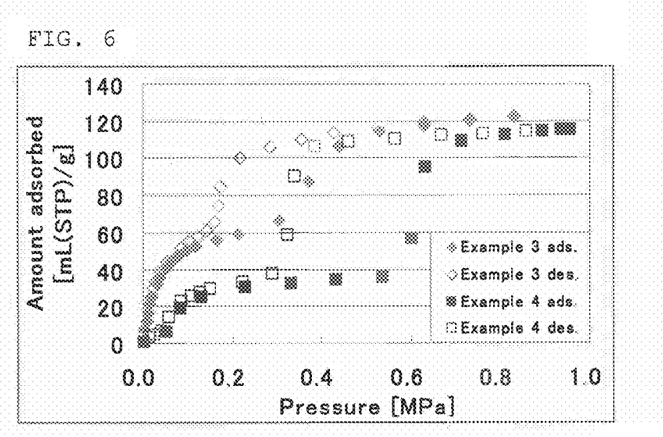
FIG. 6 The results of measuring, by using the volumetric method, an adsorption/desorption isotherms for carbon dioxide at 273 K of the metal complexes obtained in Synthesis Example 1 and Synthesis Example 2.

An adsorption/desorption isotherm for carbon dioxide at 273 K of the metal complex obtained in Synthesis Example 1 was measured based on the volumetric method. The results are shown in FIG. 6.

Example 4

An adsorption/desorption isotherm for carbon dioxide at 273 K of the metal complex obtained in Synthesis Example 2 was measured based on the volumetric method. The results are shown in FIG. 6.

Comparative Example 3

An adsorption/desorption isotherm for carbon dioxide at 273 K of the metal complex obtained in Comparative Synthesis Example 1 was measured based on the volumetric method. The results are shown in FIG. 7.

Comparative Example 4

An adsorption/desorption isotherm for carbon dioxide at 273 K of the metal complex obtained in Comparative Synthesis Example 3 was measured based on the volumetric method. The results are shown in FIG. 7.

Figure 7:
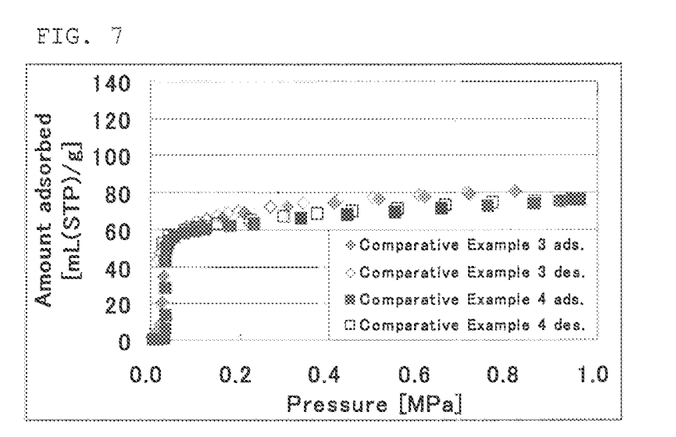
FIG. 7 The results of measuring, by using the volumetric method, adsorption/desorption isotherms for carbon dioxide at 273 K of the metal complexes obtained in Comparative Synthesis Example 1 and Comparative Synthesis Example 2.

It is apparent from FIGS. 6 and 7 that the metal complexes of the invention are excellent as a storage material of carbon dioxide because of their large equilibrium adsorption amount of carbon dioxide and in addition, their large effective adsorption amount supposing that they are taken out at ordinary pressure (0.1 MPa). The adsorption/desorption isotherm shows a hysteresis so that not only the adsorption capacity is large but also the pressure upon transport or storage can be kept low.

Example 5

Figure 8:
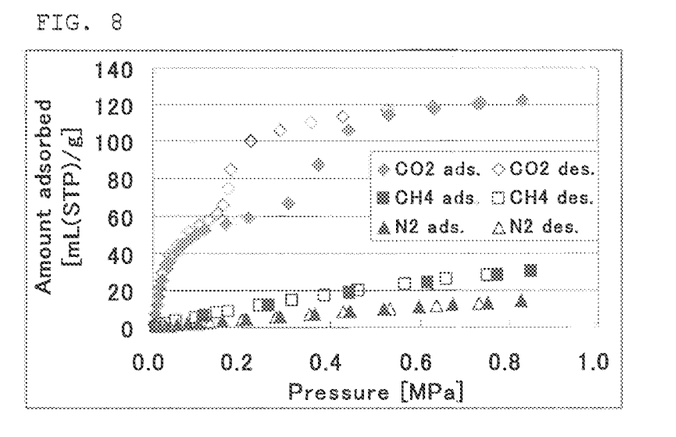
FIG. 8 The results of measuring, by using the volumetric method, adsorption/desorption isotherms for carbon dioxide, methane, and nitrogen at 273 K of the metal complex obtained in Synthesis Example 1.

Adsorption/desorption isotherms for carbon dioxide, methane, and nitrogen at 273 K of the metal complex obtained in Synthesis Example 1 was measured based on the volumetric method. The results are shown in FIG. 8.

Example 6

Figure 9:
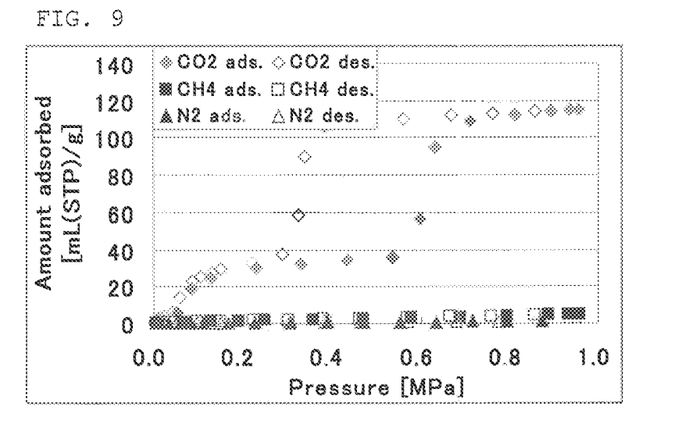
FIG. 9 The results of measuring, by using the volumetric method, adsorption/desorption isotherms for carbon dioxide, methane, and nitrogen at 273 K of the metal complex obtained in Synthesis Example 2.

Adsorption/desorption isotherms for carbon dioxide, methane, and nitrogen at 273 K of the metal complex obtained in Synthesis Example 2 was measured based on the volumetric method. The results are shown in FIG. 9.

Comparative Example 5

Figure 10:
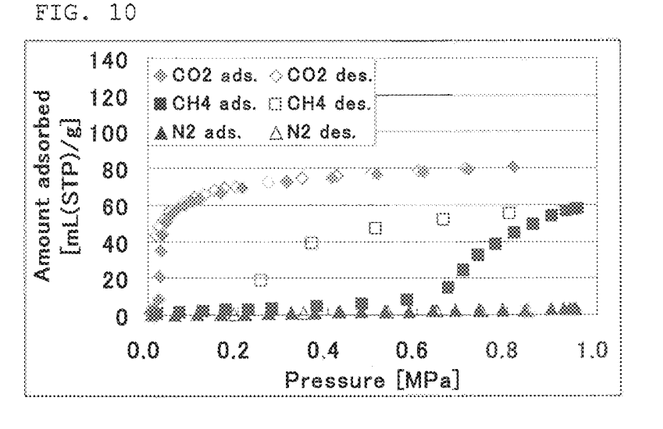
FIG. 10 The results of measuring, by using the volumetric method, adsorption/desorption isotherms for carbon dioxide, methane, and nitrogen at 273 K of the metal complex obtained in Comparative Synthesis Example 1.

Adsorption/desorption isotherms for carbon dioxide, methane, and nitrogen at 273 K of the metal complex obtained in Comparative Synthesis Example 1 was measured based on the volumetric method. The results are shown in FIG. 10.

Comparative Example 6

Figure 11:
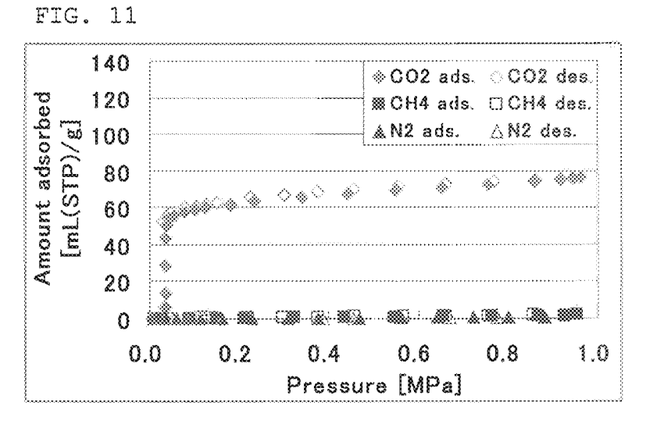
FIG. 11 The results of measuring, by using the volumetric method, adsorption/desorption isotherms for carbon dioxide, methane, and nitrogen at 273 K of the metal complex obtained in Comparative Synthesis Example 2.

Adsorption/desorption isotherms for carbon dioxide, methane, and nitrogen at 273 K of the metal complex obtained in Comparative Synthesis Example 3 was measured based on the volumetric method. The results are shown in FIG. 11.

It is apparent from FIGS. 8 to 11 that the metal complexes of the invention are excellent as a material for separating methane from carbon dioxide or nitrogen from carbon dioxide because, in separation between methane and carbon dioxide or separation between nitrogen carbon dioxide by using the pressure swing adsorption process, it selectively adsorbs thereto carbon dioxide and at the same time, adsorbs a large amount of carbon dioxide; and it does not require much energy for recovery because it can release a large amount of carbon dioxide only by returning the pressure to ordinary pressure (0.1 MPa).

Example 7

Figure 12:
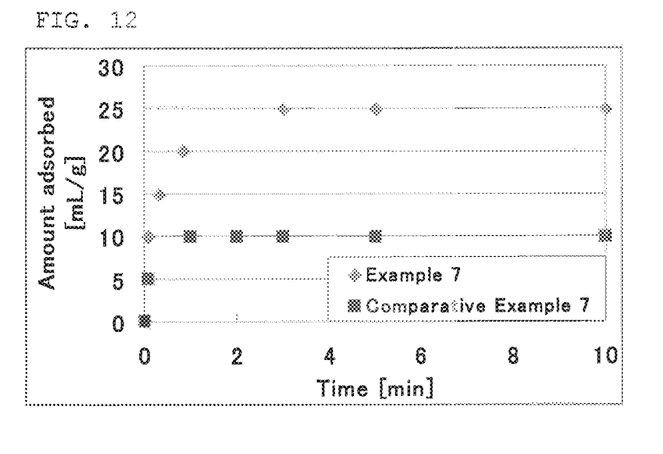
FIG. 12 A time-dependent change in an amount, at 273 K and 0.1 MPa, of a gas mixture of carbon dioxide and methane having a carbon dioxide:methane volumetric ratio of 25:75 adsorbed on the metal complexes obtained in Synthesis Example 1 and Comparative Synthesis Example 1.

With regard to the metal complex obtained in Synthesis Example 1, the time-dependent change in the adsorption amount and separation performance were measured at 273 K and 0.1 MPa by using a 25:75 (volumetric ratio) gas mixture of carbon dioxide and methane. The results are shown in FIG. 12. In the measurement, carbon dioxide selectivity was 100%.

Comparative Example 7

With regard to the metal complex obtained in Comparative Synthesis Example 1, the time-dependent change in the adsorption amount and separation performance were measured at 273 K and 0.1 MPa by using a 25:75 (volumetric ratio) gas mixture of carbon dioxide and methane. The results are shown in FIG. 12. In the measurement, carbon dioxide selectivity was 100%.

It is apparent from FIG. 12 that the metal complex of the invention is excellent as a separation material to be used in the pressure swing adsorption process because it can adsorb thereto a large amount of carbon dioxide while keeping selectivity even if the partial pressure of carbon dioxide is low.

INDUSTRIAL APPLICABILITY

The metal complex of the invention has a large adsorption capacity and exhibits an excellent gas adsorption performance so that it is preferred as an adsorbent material for adsorbing thereto carbon dioxide, hydrogen, carbon monoxide, oxygen, nitrogen, hydrocarbons having from 1 to 4 carbon atoms, noble gases, hydrogen sulfide, ammonia, sulfur oxide, nitrogen oxide, siloxanes, water vapor, or organic vapor. It can contribute to a reduction in the size of a gas adsorbing apparatus. The metal complex of the invention has a large storage amount so that it is preferred as a storing material for storing therein carbon dioxide, hydrogen, carbon monoxide, oxygen, nitrogen, hydrocarbons having from 1 to 4 carbon atoms, noble gases, hydrogen sulfide, ammonia, water vapor, or organic vapor. It can contribute to a reduction in the size of a gas storage apparatus. Further, the metal complex of the invention is capable of selectively adsorbing thereto various gases by controlling an adsorption pressure so that it is preferred as a material for separating carbon dioxide, hydrogen, carbon monoxide, oxygen, nitrogen, hydrocarbons having from 1 to 4 carbon atoms, noble gases, hydrogen sulfide, ammonia, sulfur oxide, nitrogen oxide, siloxanes, water vapor, or organic vapor. It can contribute to a reduction in size of a gas separation apparatus. In particular, it is preferred as a material for separating methane from carbon dioxide, hydrogen from carbon dioxide, nitrogen from carbon dioxide, or carbon dioxide from air.

REFERENCE SIGNS LIST

STP: Standard Temperature and Pressure
ads.: adsorption
des.: desorption

The invention claimed is:

1. A metal complex comprising:
an aromatic dihydroxy monocarboxylic acid compound;
at least one metal selected from the group consisting of chromium, molybdenum, tungsten, manganese, iron, ruthenium, cobalt, rhodium, nickel, palladium, copper, zinc, and cadmium; and
an organic ligand capable of bidentate binding to the metal;
wherein the aromatic dihydroxy monocarboxylic acid compound is:
a compound represented by the following formula (I):

(I)

where $R^1$, $R^2$, $R^3$, $R^4$ and $R^5$ may be the same or different and each independently represents a hydrogen atom, an alkyl group which may have a substituent, an aryl group, an aralkyl group, an alkoxy group, an aryloxy group, an aralkyloxy group, an amino group, an amide group, or a halogen atom; or a compound represented by the following formula (II):

(II)

where $R^6$, $R^7$, $R^8$, $R^9$, $R^{10}$, $R^{11}$ and $R^{12}$ may be the same or different and each independently represents a hydrogen atom, an alkyl group which may have a substituent, an aryl group, an aralkyl group, an alkoxy group, an aryloxy group, an aralkyloxy group, an amino group, an amide group, or a halogen atom.

2. The metal complex according to claim 1, wherein the organic ligand capable of bidentate binding to the metal is at least one selected from the group consisting of 1,4-diazabicyclo[2.2.2]octane, pyrazine, 2,5-dimethylpyrazine, 4,4'-bipyridyl, 2,2'-dimethyl-4,4'-bipyridine, 1,2-bis(4-pyridyl)ethyne, 1,4-bis(4-pyridyl)butadiyne, 1,4-bis(4-pyridyl)benzene, 3,6-di(4-pyridyl)-1,2,4,5-tetrazine, 2,2'-bi-1,6-naphthyridine, phenazine, diazapyrene, trans-1,2-bis(4-pyridyl)ethene, 4,4'-azopyridine, 1,2-bis(4-pyridyl)ethane, 1,2-bis(4-pyridyl)glycol, and N-(4-pyridyl)isonicotinamide.

3. The metal complex according to claim 1, wherein the aromatic dihydroxy monocarboxylic acid compound is 3,7-dihydroxy-2-naphthoic acid.

4. The metal complex according to claim 1, wherein the aromatic dihydroxy monocarboxylic acid compound is 4,4'-dihydroxy-3-biphenylcarboxylic acid.

5. The metal complex according to claim 1, wherein the metal is copper.

6. An adsorbent material comprising the metal complex as claimed in claim 1.

7. The adsorbent material according to claim 6, which is an adsorbent material for adsorbing thereto carbon dioxide, hydrogen, carbon monoxide, oxygen, nitrogen, hydrocarbons having from 1 to 4 carbon atoms, noble gases, hydrogen sulfide, ammonia, sulfur oxide, nitrogen oxide, siloxanes, water vapor, or organic vapor.

8. A storage material comprising the metal complex as claimed in claim 1.

9. The storage material according to claim 8, which is a storage material for storing therein carbon dioxide, hydrogen, carbon monoxide, oxygen, nitrogen, hydrocarbons having from 1 to 4 carbon atoms, noble gases, hydrogen sulfide, ammonia, water vapor, or organic vapor.

10. A separation material comprising the metal complex as claimed claim 1.

11. The separation material according to claim 10, which is a separation material for separating carbon dioxide, hydrogen, carbon monoxide, oxygen, nitrogen, hydrocarbons having from 1 to 4 carbon atoms, noble gases, hydrogen sulfide, ammonia, sulfur oxide, nitrogen oxide, siloxanes, water vapor, or organic vapor.

12. The separation material according to claim 10, which is a separation material for separating methane from carbon dioxide, hydrogen from carbon dioxide, nitrogen from carbon dioxide, or carbon dioxide from air.

13. A method of manufacturing the metal complex as claimed in claim 1, comprising:

reacting, in a solvent, the aromatic dihydroxy monocarboxylic acid compound, at least one metal salt selected from the group consisting of chromium salt, molybdenum salt, tungsten salt, manganese salt, iron salt, ruthenium salt, cobalt salt, rhodium salt, nickel salt, palladium salt, copper salt, zinc salt, and cadmium salt, and the organic ligand capable of bidentate binding to the metal to cause precipitation.

* * * * *